United States Patent [19]
Beal et al.

[11] Patent Number: 5,738,110
[45] Date of Patent: Apr. 14, 1998

[54] DEVICE FOR THE DIAGNOSIS OF CERTAIN GASTROINTESTINAL PATHOGENS

[76] Inventors: Charles B. Beal, 1312 Bellair Way, Menlo Park, Calif. 94025; Leonard O. Ross, 799 Wolfe Rd., Sunnyvale, Calif. 94086; Mark A. Hughes, 4524 Felter Rd., Milpitas, Calif. 95035

[21] Appl. No.: 655,029

[22] Filed: May 29, 1996

[51] Int. Cl.$^6$ .................................................. A61B 10/00
[52] U.S. Cl. .......................... 128/769; 128/780; 604/327
[58] Field of Search ................................ 128/760, 762, 128/768, 769, 780; 604/93, 317, 327, 328, 358

[56] References Cited

U.S. PATENT DOCUMENTS

| | | | |
|---|---|---|---|
| 2,773,502 | 12/1956 | Kaslow et al. | 128/260 |
| 3,528,429 | 9/1970 | Beal et al. | 128/2 |
| 3,683,890 | 8/1972 | Beal | 128/2 |
| 4,481,952 | 11/1984 | Pawelec | 128/769 |

OTHER PUBLICATIONS

G.H. Rabbani, R.H.Gilman, A.Islam, J.Froelich, Comparison of String–test and Stool Examination in the Diagnosis of Strongyloidiasis and Giardiasis in Gastroenteritis Patients; Asian Medical Journal, vol. 25, pp. 695–700, No. 9, Sep. 1982.

E.Perez–Trallero, M.Montes, M.Alcorta, P.Zubillaga, E.Telleria, Non–endoscopic method to obtain *Helicobacter pylori* for culture; vol. 345, Mar. 11, 1995.

K.R.Kamath, M.D., R.Murugasu, A Comparative Study of Four Methods for Detecting Giardia Lamblia in Children with Diarrheal Disease and Malabsorption; Gastroenterology 66; 16–21, 1974.

S.M.Riordan, C.J.McIver, V.M.Duncombe, T.D. Bolin; An appraisal of a "String test" for the detection of small bowel bacterial overgrowth; Journal of Topical Medicine and Hygiene, pp. 117–120, 1995.

M.E.Whiteside, J.S.Barkin, R.G.May, S.D.Weiss, M.A.Fischi, C.L.MacLeod; Enteric Coccidiosis Among Patients with the Aquired Immunodeficiency Syndrome; American Tropical Medicine, Hyg. 33(6) pp. 1065–1072, 1984.

L.Benavente, E.Gotuzzo, J.Guerra, O.Grados, H.Guerra, N.Bravo; Diagnosis of typhoid fever using a string capsule device; Transactions of the Royal Society of Tropical Medicine and Hygiene, vol. 78, pp. 404–406, 1984.

R.H. Gilman; S.Islam, H.Rabbani, H.Ghosh; Identification of Gallbladder Typhoid Carriers By A String Device; The Lancet, Apr. 14, 1979, p. 795.

R.Gilman, R.B.Hornick; Duodenal Isolation of *Salmonella typhi* By String Capsule In Acute Typhoid Fever; Journal of Clinical Microbiology, Apr. 1976, p. 456–457.

S.S.Gellos, The Pediatric Entero–Test for Giardiasis; The Weekly Pediatric Commentary; vol. 4, No. 10, Mar. 5, 1980.

B.Bezjak,M.D.; Evaluation of a New Technic for Sampling Duodenal Contents in Parasitologic Diagnosis; American Journal of Digestive Diseases, pp. 848–850, 1972.

(List continued on next page.)

*Primary Examiner*—Vincent Millin
*Assistant Examiner*—Robert N. Wieland
*Attorney, Agent, or Firm*—Lyon & Lyon LLP

[57] ABSTRACT

A device for the diagnosis of certain gastrointestinal pathogens includes a gelatin pharmaceutical capsule which contains a malleable drag material made of a mixture of beeswax and mineral oil. Embedded in the drag material is a narrow piece of thin sampling cloth with inwardly tapered ends. The free end of the sampling cloth is attached to a string which extends through a perforation in the capsule. The patient holds the free end of the string and swallows the capsule. The sampling cloth and drag material are retrieved for testing after the capsule is digested.

15 Claims, 4 Drawing Sheets

OTHER PUBLICATIONS

S.Hoffman, R.Rockhill, A.Rivai, S.Pulungsih; Duodenal String–Capsule Culture Compared with Bone–Marrow, Blood, and Rectal–Swab Cultures for Diagnosing Typhoid and Paratyphoid Fever; The Journal of Infectious Diseases, vol. 149, No. 2, Feb. 1984.

J.Jones, M.D.,MS; String Test for Diagnosing Giardiasis; American Family Physician, vol. 34, No. 2, Aug. 1986.

P.Rosenthal, M.D., W.Liebman, M.D.; Comparative Study of Stool Examinations, Duodenal Aspiration, and Pediatric Entero–Test for Giardiasis in Children; The Journal of Pediatrics, vol. 96, No. 2 pp. 278–279, Feb. 1980.

C.Beal, P.Viens, R.Grant, J.Hughes, A New Technique for Sampling Duodenal Contents; The American Journal of Tropical Medicine and Hygiene, vol. 19, No. 2, pp. 349–352, Mar. 1970.

L.Benavente, E.Gotuzzo, J.Guerra, A.vonHumboldt, O.Grados, H.Guerra; Diagnosis of *Salmonella typhi* by Culture of Duodenal String Capsule; New England Journal of Medicine, p. 54, Jan. 1, 1981.

A.Bussalleu, J.Guerra, A.Nago, J.Watanabe, R.Espinoza, Endoscopic Findings after String–Capsule test (letter to editor); Digistive Diseases and Sciences, vol. 30, No. 4, Apr. 1985.

A.Avendano, P.Herrera, I.Horwitz, E.Duarte, I.Prenzel, C.Lanata, M.Levine; Duodenal String Cultures: Practicality and Sensitivity for Diagnosing Enteric Fever in Children; The Journal of Infectious Diseases, vol. 153, No. 2, pp. 359–362, Feb. 1986.

D.Raoult, J.Delmont, B.Xeridat, H.Gallais, P.Casanova; Le String–test Dans Le Giagnostic De La Fièvre Typhoïde, La Presse Médicale, Dec. 8, 1984, vol. 13 No. 44.

W.Liebman, P.Rosenthal, The Sting Test for Gastroesophageal Reflux; American Journal Dis. Child; vol. 134, Aug. 1980.

P.Rosenthal; Collection of Duodenal Bile in Infants and Children by the String Test; Journal of Pediatric Gastroenterology and Nutrition; Article 4171; Feb. 13, 1985.

G.Thomas J.Goldsmid, A.Wicks; Use of the Enterotest Duodenal Capsule in the Diagnosis of Giardiasis; S.A. Medical Journal, vol. 48, Nov. 2, 1974, pp. 2219–2220.

Advertisement; Entero–Test, Date Unknown.

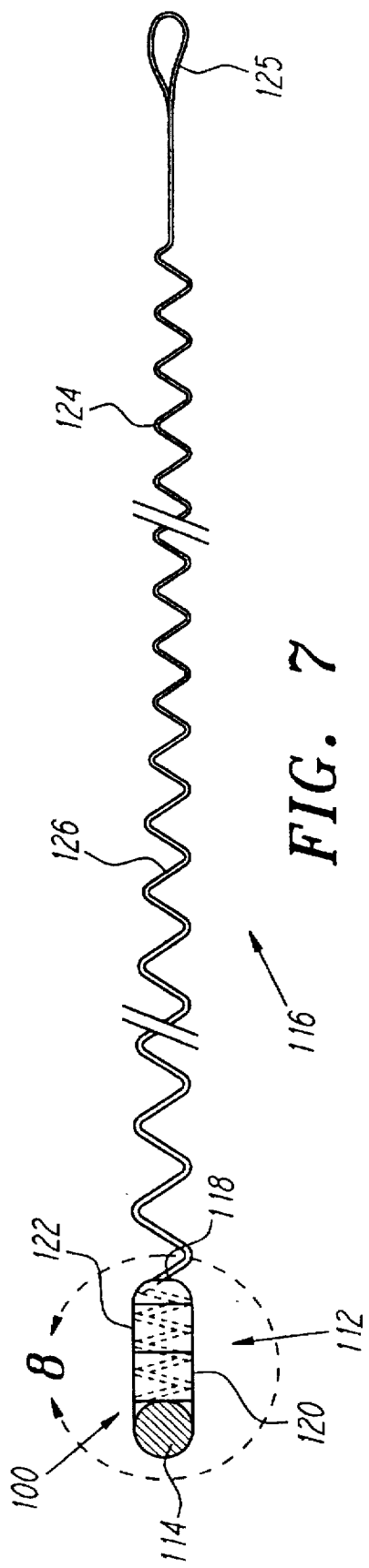
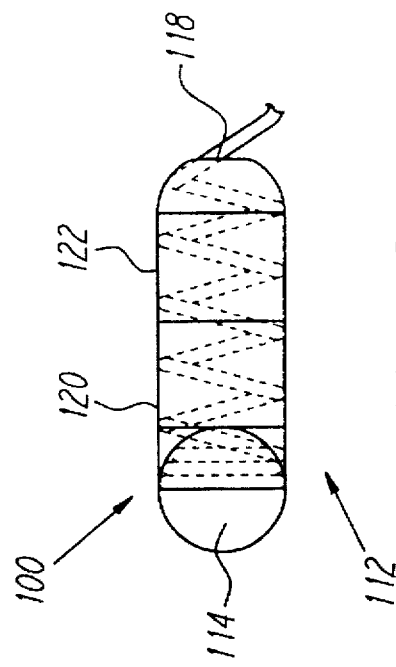
FIG. 7
FIG. 8

DEVICE FOR THE DIAGNOSIS OF CERTAIN GASTROINTESTINAL PATHOGENS

BACKGROUND OF THE INVENTION

1. Field of the Invention

The present invention pertains to the field of gastrointestinal sampling.

2. Background of the Invention

Gastrointestinal sampling can be accomplished by performing gastroscopy with biopsy. However, such sampling can also be done less expensively and less invasively through the use of a digestible pharmaceutical capsule containing an extractable line. Using such an apparatus, the patient holds a free end of the line before swallowing the capsule. The line plays out of the capsule as the capsule travels through the patient's esophagus until the capsule enters the patient's stomach. The capsule then either dissolves or passes through the patient's digestive system, leaving the line within the stomach. After a certain period of time, the line is eventually pulled out by the patient. That end of the line that was once within the capsule but which played out into the stomach is subsequently tested for the presence of various microorganisms or gastrointestinal bleeding. Such a method and apparatus is disclosed in U.S. Pat. No. 3,528,429 and Canadian Patent No. 802,858, both of which are fully incorporated herein by reference.

Another known technique is to use an outer, dissolvable capsule that encloses an inner capsule that is weighted with lead weight. The lead weight enables the line to drag against the inner lining of the stomach to enhance the sampling. The inner capsule is coated inside with silicone rubber, which collapses into a flexible bag upon dissolution of the outer capsule. The bag then passes through the pylorus of the stomach into the duodenum. When pulled from the patient, the line detaches from the bag, and the bag with the weight eventually passes with the patient's stool. While this apparatus has advantages over other systems, the absorptive surface of the line used with this technique is not large enough to collect a sufficient number of epithelial cells without dragging against the inner wall of the stomach. Moreover, the device is relatively expensive because two capsules, a flexible bag and a lead weight are required. This method and apparatus is disclosed in U.S. Pat. No. 3,683,890, the entirety of which is incorporated herein by reference.

Another prior art device has a steel ball that is nondetachably connected to the line. The steel ball promotes the dragging of the line against the inner lining of the stomach, which enhances sampling of epithelial cells. In use, the patient swallows the capsule. When the capsule enters the stomach, it either melts, dissolves or breaks apart and passes through the digestive system. After an indwelling period, the line is pulled out of the stomach, through the esophagus and out of the mouth. Like other prior art apparatus, this system has advantages. However, when pulling the line from the stomach, resistance from the gastroesophageal sphincter can be encountered when the steel ball passes through it. The resistance caused by this encounter with the gastroesophageal sphincter can cause discomfort to the patient, and in some cases, can damage it. This method and apparatus is disclosed in U.S. Pat. No. 2,773,502, the entirety of which is incorporated herein by reference.

In recent years, newly discovered bacteria such as *Helicobacter pylori* ("*H.pylori*") have been shown to be associated with benign gastric and duodenal ulcers, as well as gastric cancer. These organisms tend to live under the gastric mucus and between the epithelial cells of the stomach. Further, these types of organisms are usually most heavily concentrated in lower portions (i.e., the antrum) of the stomach. Prior art devices such as those discussed above have difficulty receiving enough organisms from these locations for proper diagnostic testing.

Prior art methods for recovering the *H.pylori* bacterium include gastroscopy with biopsy (as mentioned above) and the prior art devices discussed above. When gastroscopy with biopsy are performed, the culture from the recovered bacteria are placed in a nutrient medium selected for the particular organism. Diagnostic testing then takes place. Gastroscopy with biopsy is an expensive, invasive and uncomfortable diagnostic procedure, as it requires the patient to orally receive an endoscope through the nose or mouth. The endoscope then passes through the esophagus and into the stomach. Once in the stomach, the biopsy forceps of the endoscope can be positioned under the gastric mucus and encompassing some of the epithelial cells of the stomach, where a biopsy is then taken. After biopsy, the endoscope must be removed from the patient. Each of these steps leads to serious patient discomfort. Thus, this procedure is generally performed while the patient is either under general anesthesia or significant sedation. Further, while gastroscopy has the benefit of allowing the operator to inspect the gastrointestinal mucosa, which would allow the operator to detect ulcerations and/or malignancies, such diseases are uncommon, especially in younger patients. If a lower cost and less invasive procedure were to be available that accurately detected the presence of *H.pylori* organisms, gastroscopy with biopsy would be unnecessary for many patients.

Thus, there are other prior art diagnostic methods available to detect the presence of these types of bacteria. One prior art method is to perform an immunoassay for the detection of the antihelicobacter antibody in the patient's blood. Another prior art method is to analyze the patient's breath using the urea breath test. In the breath test, the patient is orally administered $C^{13}$ or $C^{14}$ type urea. H.pylori, which produces urease, will break down the urea to ammonia and carbon dioxide if it is present in the stomach. The breath test then measures the amount of $C^{13}$ or $C^{14}$ carbon dioxide in the patient's breath. If $C^{13}$ or $C^{14}$ is detected in the patient's breath, the patient is determined to have *H.pylori* bacteria present in the stomach. The antibody detection test is not highly accurate because it cannot determine whether any *H.pylori* bacteria are actually residing in the stomach. The breath test sometimes detects the presence of urease producing bacteria other than H.pylori. Further, since these methods do not actually recover a sample of the bacterium in the stomach, it is possible the organisms being tested for will not be present, but others that these tests do not react to, will be present.

Thus, as can be seen, none of these prior art devices and methods provide for an inexpensive, non-invasive diagnostic procedure that allows for the recovery of significant samples from under the gastric mucus and between the epithelial cells of the stomach. If such devices and methods were available, organisms such as *H.pylori* could be quickly, inexpensively and non-invasively detected in patients. Once detected, antibiotics having efficacy against those bacteria could be administered with the expectation that the patient will become symptom free.

Thus, based upon the foregoing, there is a need for a relatively inexpensive gastrointestinal sampling device that enhances sampling without contributing added discomfort to the patient.

SUMMARY OF THE INVENTION

The present invention is directed to a gastrointestinal sampling apparatus that increases the number of epithelial cells removed from the stomach lining without causing additional discomfort to the patient and which is particularly useful for obtaining samples from under the gastric mucus and between the epithelial cells of the stomach. To these ends, a device for the diagnosis of certain gastrointestinal pathogens comprises a capsule containing a drag material. Embedded in the drag material is a line which runs through an opening in the capsule.

In a first, separate aspect of the present invention, the drag material is malleable. In one embodiment, the drag material may be made of a mixture of beeswax and mineral oil in proportions to render the material easily malleable at body temperature, but firm enough to maintain its mass against moderate resistance.

In a second, separate aspect of the present invention, a malleable drag material embeds the line, which is composed of a string segment attached to a cloth portion, the cloth portion embedded in the drag material and the string segment running through the opening in the capsule.

Accordingly, it is an object of the present invention to provide a gastrointestinal sampling device that is both more efficient and more accurate yet does not sacrifice patient comfort. Other and further objects and advantages of the present invention will appear hereinafter.

BRIEF DESCRIPTION OF THE DRAWINGS

FIG. 7 is a diagrammatic view in section of an alternative embodiment of the invention.

FIG. 8 is an enlarged diagrammatic view in section of the alternative embodiment of the present invention shown in FIG. 7.

DETAILED DESCRIPTION OF THE PREFERRED EMBODIMENTS

Figure 1:
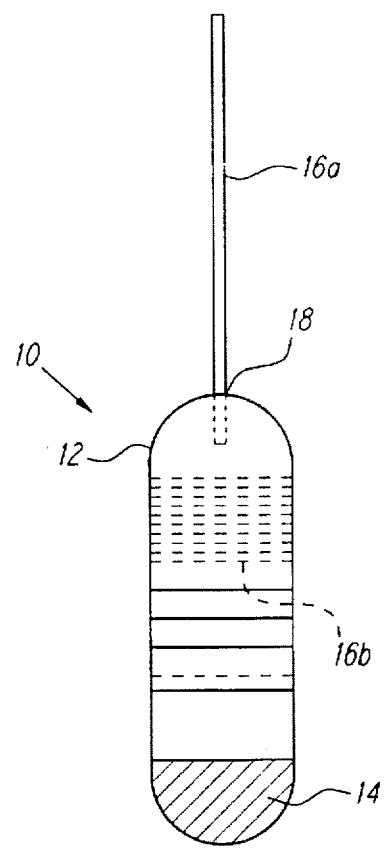
FIG. 1 is a front side view of a gastrointestinal sampling device.

Turning in detail to the drawings, FIG. 1 illustrates a device according to the instant invention. A gastrointestinal sampling device 10 includes a capsule 12. The capsule 12 is preferably of size 000. The capsule 12 contains a malleable drag material 14 situated adjacent an end of the capsule 12. Connected to the drag material 14 is a line 16 also inside the capsule 12. The line 16 runs through an opening or perforation 18 in an end of the capsule 12 opposite the drag material 14. As shown, part of the line 16a extends outside the capsule 12, and the rest of the line 16b is tightly wound or randomly packed in a cocoon-like fashion, as described below.

Figure 2:
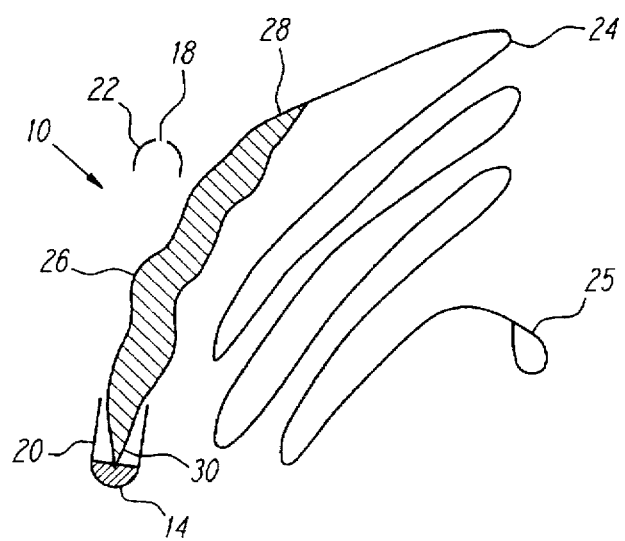
FIG. 2 is an exploded front side view of the device of FIG. 1.

FIG. 2 depicts the device of FIG. 1 in unassembled form, illustrating the device in greater detail. With reference to both FIGS. 1 and 2, it can be seen that in a preferred embodiment, the capsule 12 can be formed of two parts, a base 20 and a cap 22. Perforation 18 is located at the apex of the cap 22. The drag material 14 is placed in the nadir of base 20. The line 16 is made up of two components, a string 24 and a narrow piece of thin sampling cloth 26. The string 24 and sampling cloth 26 may also be referred to, respectively, as proximal and distal segments. The sampling cloth 26 is connected at one end to the string 24. Of course, in certain embodiments, string 24 and sampling cloth 26 could be formed from the same fabric or line material. The other end of the sampling cloth 26 is embedded in the drag material 14. The string 24 has one end free to extend through the perforation 18 when the device 10 is in the assembled form of FIG. 1. A loop 25 may be formed at the end of string 24 which extends out of perforation 18.

Figure 3:
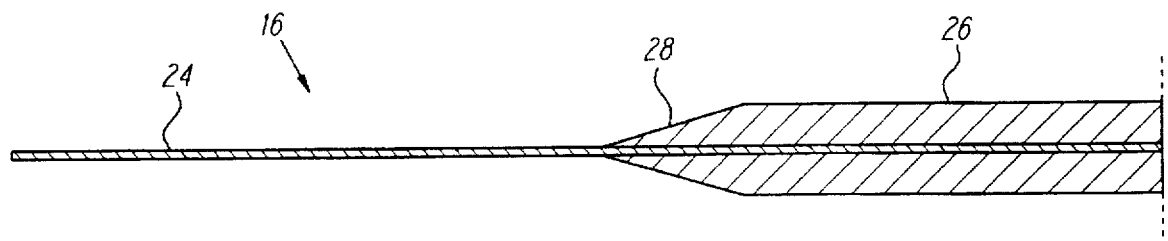
FIG. 3 is a side view of a line used in the device of FIG. 1.

The sampling cloth 26 may have inwardly tapered ends 28, 30 as shown in FIG. 3. In one embodiment, the sampling cloth 26 is roughly twenty centimeters long, approximately two centimeters wide, and is made of nylon. In one embodiment, the string 24 is roughly fifty centimeters long and is composed of nylon fibers. The capsule 12 is preferably a gelatin pharmaceutical capsule that readily dissolves when subjected to stomach acid. In a preferred embodiment, the drag material 14 is composed of a mixture of beeswax and heavy mineral oil in proportions to render the drag material 14 easily malleable at body temperature, yet firm enough to maintain its mass against moderate resistance. In a preferred embodiment, the ratio of beeswax to heavy mineral oil can be approximately 4 to 3.

The line 16 is installed within capsule 12 as follows. Line 16 is wound such that the tapered end 28 of sampling cloth 26 is located on the exterior of the winding and the string 24 is located at the interior of the winding. Such an arrangement allows for the line 16 to be pulled out of the capsule 12 without binding or snagging. After the line 16 is wound, it is placed within the cap 22 of capsule 12 with the string 24 passing through perforation 18. As base 20 is fastened to cap 22, the wound line 16 releases against the side walls of capsule 12 so that it is held in radial compression. The line 16 can also be installed in the capsule 12 by randomly packing within the capsule 12. Further, the line 16 can also be installed in capsule 12 by packing it within the capsule in an accordion-like fashion.

Embodiments of device 10 may be of various sizes and the line 16 of various lengths. The line 16, particularly the distal segment 26, may be constructed of various materials to be more or less abrasive and more or less absorptive, although maximum absorptive capacity is generally considered preferable. In one preferred embodiment, the sampling cloth 26 is constructed of the same material as the proximal segment 24 of line 16. As discussed, the proximal segment can be constructed of nylon string. To produce the sampling cloth 26, the nylon string is scraped until the coils of nylon fibers that form the string are flatted out. After the sampling cloth 26 is produced, it is woven into the proximal segment 24 and secured by an appropriate glue, preferably silicone rubber glue or heat sealed together.

The gelatin capsule 12 may be substituted with a hot gelatin dip which encases a sterilized line 16. When the gelatin cools, the line 16 can be formed as a capsule surrounded by gelatin. The gelatin used for the hand dipped capsule embodiment of the device 10 may be softer (lower durometer) than the gelatin used in standard gelatin pharmaceutical capsules USP. The drag material 14 may have variable ratios of the two components (mineral oil and beeswax), or an entirely different material—moldable or non-moldable—may be used. Or the drag material 14 may be eliminated.

In one preferred embodiment of the invention, the length of distal segment or sampling cloth 26 is increased and the width of the sampling cloth 26 is decreased such that the same volume of material fits within the capsule 12. Thus, for example, instead of using a length of twenty centimeters and a width of two centimeters for the distal segment 26, the length of the distal segment 26 would be forty centimeters and the width would be one centimeter. The advantage of an elongated distal segment 26 is that the longer sampling cloth 26 is better able to collect and facilitate detection of any bleeding that might occur within the entire length of the stomach, including the gastroesophageal junction.

To use this embodiment of the invention, several centimeters of the string 24 are withdrawn from the capsule 12 and held by the patient while the capsule 12 is swallowed. Like other medication administered orally in capsule form, swallowing the capsule is aided if the patient uses some water. While the capsule 12 descends through the esophagus and into the stomach, the line 16 plays out through the perforation 18 in the cap 22. Once the capsule 12 passes through the esophagus and the gastroesophageal sphincter, it enters the stomach, where the capsule 12 dissolves, leaving only the line 16, which is attached to the drag material 14. After approximately thirty minutes within the stomach, the line 16 is pulled up from the stomach and removed completely from the mouth. In this process the drag material 14 follows the sampling cloth 26 up along the wall of the stomach. If the gastrointestinal sphincter is unyielding, the drag material 14, which, as discussed, is malleable, molds itself to conform to whatever shape the gastrointestinal sphincter opening permits, allowing the line 16 to be retrieved with minimal discomfort.

Figure 4:
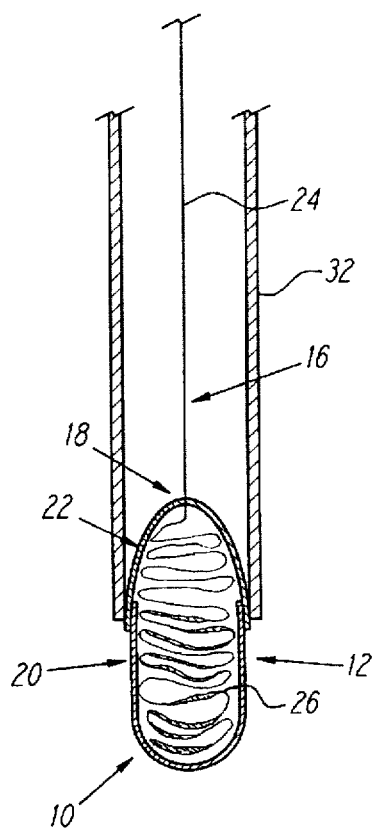
FIG. 4 is a diagrammatic view in section of a catheter-based embodiment of the present invention.
Figure 5:
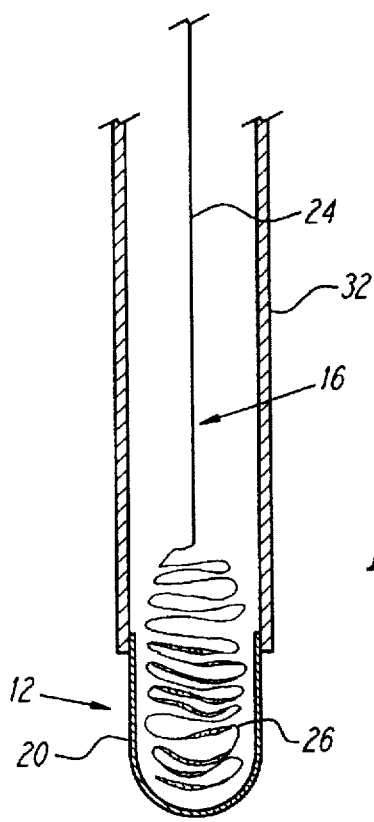
FIG. 5 is a diagrammatic view in section of an alternative catheter-based embodiment of the present invention.
Figure 6:
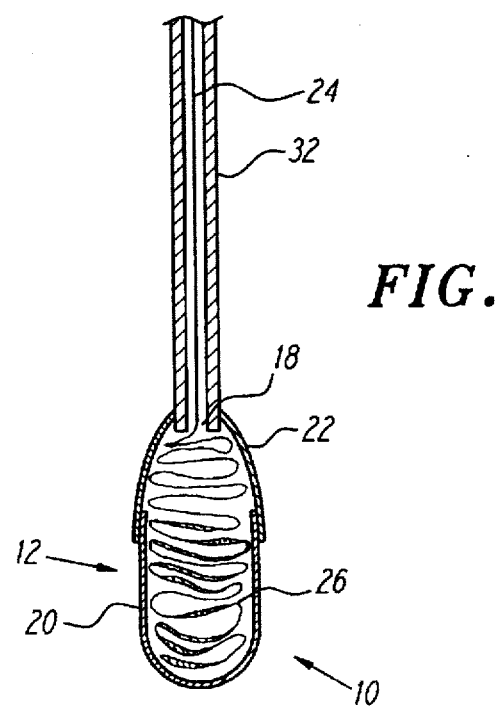
FIG. 6 is a diagrammatic view in section of an alternative catheter-based embodiment of the present invention.

With reference to FIGS. 4–6, another embodiment which provides a means to deliver the line 16 to the stomach and/or upper small bowel of an infant or other patient who is not able to swallow even a small capsule voluntarily is shown. In this embodiment, the device 10 is fitted at the distal end of a catheter 32. In such an embodiment, the base 20 of the gelatin capsule 12 may be elongated in relation to its diameter. For example, a capsule 12 that is roughly twelve millimeters long and four millimeters in diameter may be used.

In the embodiment of FIG. 4, a narrow line 16, preferably having a length of approximately twenty five centimeters is used, about fifteen centimeters of which is packed into the base 20 of the capsule 12, and about ten centimeters of which protrudes from the perforation 18 of the cap 22 and passes through the lumen of the catheter 32. In this embodiment, the cap 22 of capsule 12 is frictionally fitted within catheter 32 such that perforation 18 is axially aligned with the lumen of catheter 32. The cap 22 has a circumference such that the capsule 12 fits snugly, thereby keeping the capsule 12 in place on the tip of the catheter 32 during introduction into the stomach.

In another embodiment, which is shown in FIG. 5, the cap 22 of the capsule 12 is eliminated altogether. Thus, in this embodiment, the base 20 of capsule 12 is frictionally fitted at the distal end of catheter 32 such that it fits snugly, thereby keeping the capsule 12 in place on the tip of the catheter 32 during introduction into the stomach. Approximately ten centimeters of line 16 plays out from base 20 of capsule 12 and is threaded through the lumen of catheter 32. Approximately fifteen centimeters of line 16, including the sampling cloth 26, is packed into the base 20 of the capsule 12.

In yet another embodiment, which is shown in FIG. 6, the perforation 18 in cap 22 of capsule 12 has a diameter which is sized to fit the distal end of catheter 32. The perforation 18 in the cap 22 of the capsule 12 should be such that the catheter 32 fits snugly, keeping the capsule 12 in place on the tip of the catheter during introduction into the stomach. Again, approximately ten centimeters of line 16 is threaded through the lumen of catheter 32 while approximately fifteen centimeters of line 16, including sampling cloth 26, remain in capsule 12.

In each of the embodiments shown in FIGS. 4–6, the catheter 32 is constructed of a flexible material which can easily move through the esophagus and into the stomach. Such materials include silicone rubber and polyurethane. The catheter 32 used in these embodiments generally have an outer diameter of 2–3 mm (French size 7–9), though they may be smaller or larger.

To use the various embodiments of FIGS. 4–6, the capsule 12 is affixed to catheter 32 in one of the various methods shown above. The base 20 of the capsule 12 may be moistened to soften it, thereby aiding introduction into the patient. The catheter 32, with the capsule 12 affixed to its tip, is then introduced into the patient orally and passed through the esophagus, the gastrointestinal sphincter and into the stomach. After the capsule 12 enters the stomach, the catheter 32 is removed by the operator by pulling it over the line 16, during which time the capsule 12 and line 16, including sampling cloth 26, remain within the stomach, except that the free end of the line 16 protrudes out of the mouth and can be removably affixed to the patient's face or other surface until the line 16 is removed. Once within the stomach, the capsule 12 softens, allowing the device 10 to separate easily from the catheter.

The sampling cloth 26 has a greater absorptive surface than that of a string, which enhances the number of epithelial cells collected. Moreover, the drag material 14 tends to produce some resistance to retrieval of the line 16. This resistance forces the sampling cloth 26 to drag against the gastrointestinal epithelial tissue, thereby allowing for the collection of a greater number of epithelial cells than previously possible.

The collected cells and mucoid material may be scraped off of the sampling cloth 26 and examined microscopically for the presence of red and white blood cells and various parasites. The removed material may alternatively be placed in culture media favoring growth and identification of such bacteria as *Salmonella typhi* and *Helicobacter pylori*. Thus, a culture-augmented immunoassay may be performed in which some of the material obtained from the sampling cloth 26 is scraped onto an immunoassay device, diluent is added, and the device is observed for color change indicating the presence of the *H.pylori* antigen. If such presence is not indicated, there may be too few organisms in the sample to produce a positive reaction in the immunoassay device. A culture is therefore initiated to increase the likelihood of a correct diagnosis. A culture medium containing urea and a pH indicator may be used. The medium changes color in the presence of urease produced by *H.pylori* because the urease reacts with urea to form ammonia, which has a basic pH. In practice, the sampling cloth 26 is placed in a liquid medium, or on the surface of a solid or semisolid medium. A color change should be observed in two to twenty-four hours if *H.pylori* is present. The use of a liquid medium allows testing of the organism for antibiotic sensitivity or for DNA fingerprinting if indicated. The culture should be incubated at about thirty-six degrees celsius to enhance reproduction of *H.pylori* organisms. A second, subsequent immunoassay device is then used with enhanced likelihood of a correct diagnosis—whether positive or negative.

After the device 10 is swallowed by the patient, the capsule 12 enters the stomach, and the sampling cloth 26 is released, it is possible that the distal tip of the sampling cloth 26 could pass through the pylorus of the stomach and into the duodenum. Unlike the stomach, contents of the duodenum tend to be alkaline and therefore have a basic pH. When the sampling cloth 26 is withdrawn from the patient, the distal tip of the sampling cloth 26 passes through the stomach, the gastrointestinal sphincter, the esophagus and out of the patient. The stomach acid typically will not neutralize the alkaline pH of the distal tip of the sampling cloth 26 that was within the duodenum. Thus, if the pH test described above where administered to the sampling cloth 26, a basic pH would be found. The basic pH, however, resulted from the alkaline duodenum and not necessarily from the *H.pylori's* reaction to the urea in the culture medium. Thus, a false positive test could result.

To prevent false positive test results, the pH of the sampling cloth 26 should be tested before it is placed in the culture medium containing urea. If a portion of the sampling cloth 26 shows a basic pH, that portion of the sampling cloth 26 should be cut off before placing it in the culture medium. This should eliminate the risk of a false positive test result. However, if it is not feasible to cut off the portion of the sampling cloth 26 that has a basic pH, the sampling cloth 26 could be neutralized using known techniques such as applying diluted hydrochloric or acetic acid.

Reference is made to FIGS. 7-8, in which an alternative embodiment of the present invention is shown. This embodiment 100 comprises a capsule 112, which is preferably formed of two parts, a base 120 and a cap 122. Perforation 118 is located at the apex of the cap 22. Line 116 is made up of two components, a string 124 and a narrow piece of thin sampling cloth 126. The sampling cloth 126 is connected at one end to the string 124. Of course, in certain embodiments, string 124 and sampling cloth 126 can be formed from the same fabric or line material. String 124 has one end free to extend through perforation 118 when the embodiment 100 is assembled. A loop 125 may be formed at the end of string 124 which extends out of perforation 118. In this embodiment, the inner surface of the capsule 112 may be coated with a flexible, water-insoluble substance such as silicone rubber (not shown). However, the inner surface of the capsule 112 may remain un-coated. Such a coating, if present, could aid the line 116 in passing into the duodenum. Further, if the inner surface of the capsule 112 is coated, a small metal ball 114 may be incorporated into the coating at the base 120 of the capsule 112 to serve as a weight. The metal ball 114 could be used as an alternative to the malleable beeswax/mineral oil drag material 14 discussed above. In one embodiment, sampling cloth 126 may be unattached to metal ball 114. In a second embodiment, sampling cloth 126 may be removably attached to metal ball 114 by covering it with a thin coating of a material such as a malleable drag material like the beeswax-mineral oil combination discussed above. During construction of this embodiment, the distal end of the sampling cloth is embedded within the malleable drag material. When the string 116 of this embodiment is removed from the patient, the metal ball 114 may pass through the gastroesophageal sphincter or it may separate from the malleable drag material and eventually be eliminated in the patient's stool.

In another embodiment of the present invention, the sampling cloth 26 may be coated with a metallic ion (not shown) and the string 24 will be a conductive material coated with a non-conductive insulation material such as silicone rubber. In a preferred embodiment, the metallic ions are silver ions. In use, an electrode (not shown) is attached externally to the patient's skin. In this embodiment, the silver coating on the sampling cloth 26 may act as an anode while the electrode which was fastened to the patient's skin acts as a cathode. Both lines are attached to a power supply capable of providing low levels of direct current. This current will liberate silver ions from the sampling cloth 26 and place them within the stomach. These silver ions are bacteriocidal and have the ability to kill H.pylori and other bacteria present in the stomach without damaging gastric epithelial cells or other tissues. Thus, in this embodiment, a gastrointestinal sampling and antibiotic device is disclosed.

Thus, a gastrointestinal sampling device is disclosed which provides increased efficiency and accuracy without sacrificing patient comfort. While embodiments and applications of this invention have been shown and described, it would be apparent to those skilled in the art that many more modifications are possible without departing from the inventive concepts herein. The invention, therefore, is not to be restricted except in the spirit of the appended claims.

What is claimed is:

1. A gastrointestinal sampling device, comprising:

a dissolvable pharmaceutical capsule having a perforated opening;

a malleable drag material within the capsule; and a line embedded in the drag material and running through the perforated opening of the capsule.

2. The device of claim 1, wherein said line comprises proximal and distal segments, said distal segment having a first end embedded in said drag material and a second end connected to said proximal segment, said proximal segment running through said perforated opening of said capsule.

3. The device of claim 2, wherein said distal segment is made of cloth, and said proximal segment is made of string.

4. The device of claim 3, wherein said first and second ends of said distal segment are inwardly tapered toward said drag material and said proximal segment, respectively.

5. The device of claim 3, wherein said distal segment is approximately twenty centimeters long and approximately two centimeters wide, and said proximal segment is approximately fifty centimeters long.

6. The device of claim 2, wherein said malleable drag material comprises beeswax and mineral oil.

7. The device of claim 2, wherein said malleable drag material comprises beeswax and mineral oil mixed in a ratio of approximately 4 to 3, respectively.

8. The device of claim 2, wherein said drag material is composed of a mixture of beeswax and mineral oil in proportions to render the drag material easily malleable at body temperature, but firm enough to maintain its mass against moderate resistance.

9. The device of claim 2 wherein said distal segment has substantially greater width than said proximal segment.

10. The device of claim 9 wherein said distal segment is made from the same material as said proximal section.

11. The device of claim 4 wherein said line is wound such that said first end of said distal segment is located at an outer circumference of said proximal portion of said line.

12. A gastrointestinal sampling device, comprising:

a dissolvable pharmaceutical capsule including a base and a cap removable from the base, the cap having a perforated apex, the base defining an internal storage area;

a malleable drag material contained in the internal storage area of the base;

an elongate cloth within the capsule and having first and second ends, the first end connected to the drag material; and a string connected to the second end of the elongate cloth, the string running through the perforated opening.

13. A gastrointestinal sampling and antibiotic device, comprising:

a dissolvable pharmaceutical capsule including a base and a cap removable from the base, the cap having a perforated apex, the base defining an internal storage area;

a malleable drag material contained in the internal storage area of the base;

a sampling cloth within the capsule and having first and second ends, the first end connected to the drag material, the sampling cloth comprising metallic ions having efficacy against bacteria disposed thereon; and a string connected to the second end of the sampling cloth, the string comprising an electrical conductor in electrical communication with the metallic ions and a non-conductive insulative covering, the string extending through the perforated opening.

14. The gastrointestinal sampling and antibiotic device of claim 13 wherein the metallic ions are silver ions.

15. The gastrointestinal sampling and antibiotic device of claim 13 wherein the metallic ions have efficacy against Helicobacter pylori but will not damage gastric epithelial cells.

* * * * *